United States Patent [19]

Lee

[11] Patent Number: 5,059,120

[45] Date of Patent: Oct. 22, 1991

[54] DENTAL IMPRESSION PADS AND METHOD OF MANUFACTURE

[76] Inventor: Robert L. Lee, 22937 Grand Terrace Rd., Colton, Calif. 92324

[21] Appl. No.: 453,418

[22] Filed: Dec. 19, 1989

[51] Int. Cl.[5] .............................................. A61C 9/00
[52] U.S. Cl. ..................................... 433/37; 433/48; 433/71
[58] Field of Search ..................... 433/37, 40, 42, 71, 433/214, 48

[56] References Cited

U.S. PATENT DOCUMENTS

| | | | |
|---|---|---|---|
| 1,663,695 | 3/1928 | Foster, Jr. | 433/48 |
| 3,228,107 | 1/1966 | Zandberg | 433/71 |
| 3,302,289 | 2/1967 | Spaulding | 433/214 |
| 4,375,966 | 3/1983 | Freeman | 433/37 |
| 4,543,062 | 9/1985 | Lee | 433/42 |
| 4,569,342 | 2/1986 | von Nostitz | 433/37 |
| 4,693,683 | 9/1987 | Lee | 433/37 |
| 4,776,792 | 10/1988 | Wagner et al. | 433/71 |

FOREIGN PATENT DOCUMENTS

| | | | |
|---|---|---|---|
| 3635817 | 2/1988 | Fed. Rep. of Germany . | |
| 3640524 | 6/1988 | Fed. Rep. of Germany | 433/71 |
| 3810907 | 10/1988 | Fed. Rep. of Germany . | |
| 2545716 | 11/1984 | France . | |
| 1324666 | 7/1987 | U.S.S.R. . | |

Primary Examiner—Paul J. Hirsch
Attorney, Agent, or Firm—Knobbe, Martens, Olson & Bear

[57] ABSTRACT

A dental impression pad is used with a dental tray for making an impression of a patient's teeth. Dental impression material, which becomes moldable when heated, is placed on one side of a strip of Mylar ® material. The other side of the strip is covered with adhesive attaching the strip the dental tray. The dental impression pad also includes a protective sheet mounted to cover and protect the adhesive until use. When the pad is used, the protective sheet is peeled away to expose the adhesive. Dental impression pads are made by applying adhesive and a protective sheet to backing strips; melting a dental impression material; dripping or placing the dental impression material on the backing strips; shaping the dental impression material to the form desired; and cooling the impression material to a hardened state.

48 Claims, 7 Drawing Sheets

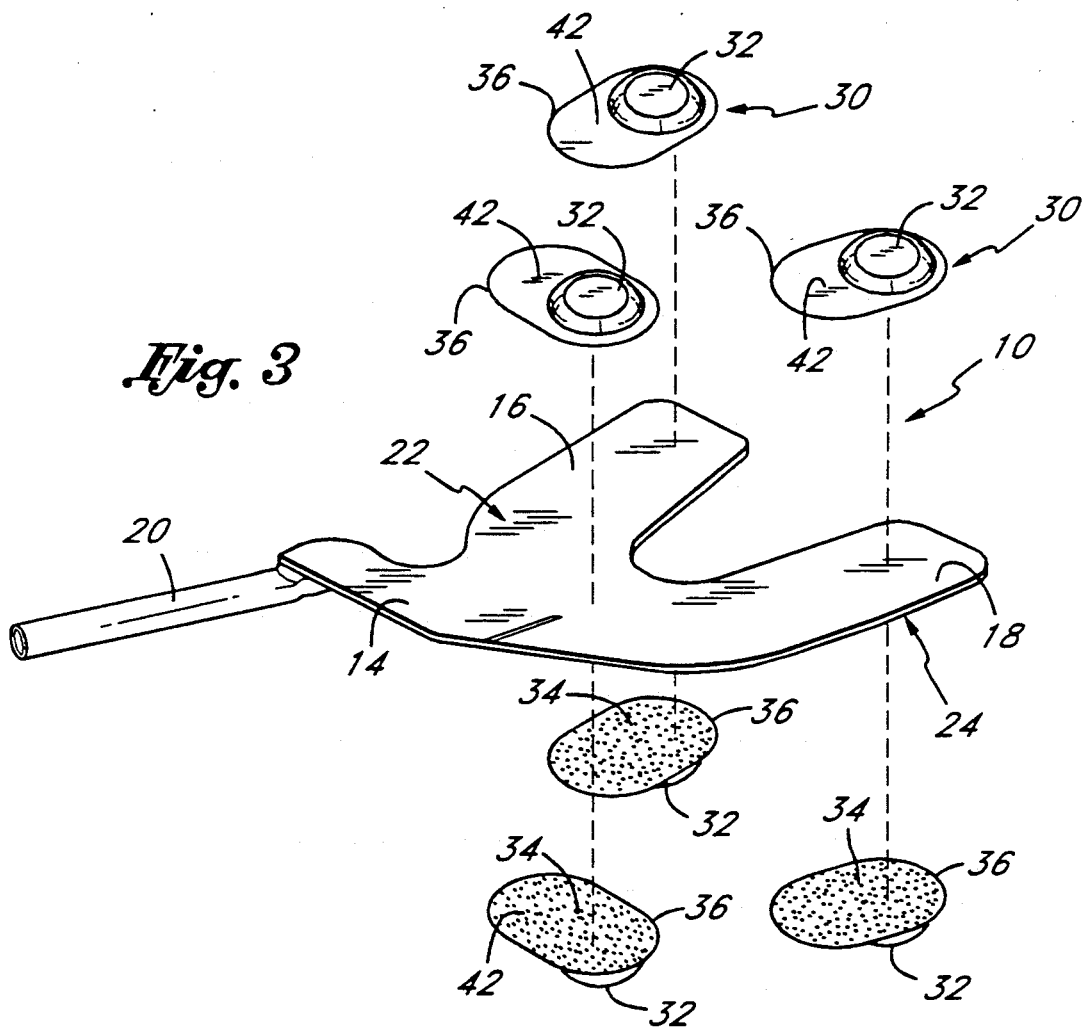
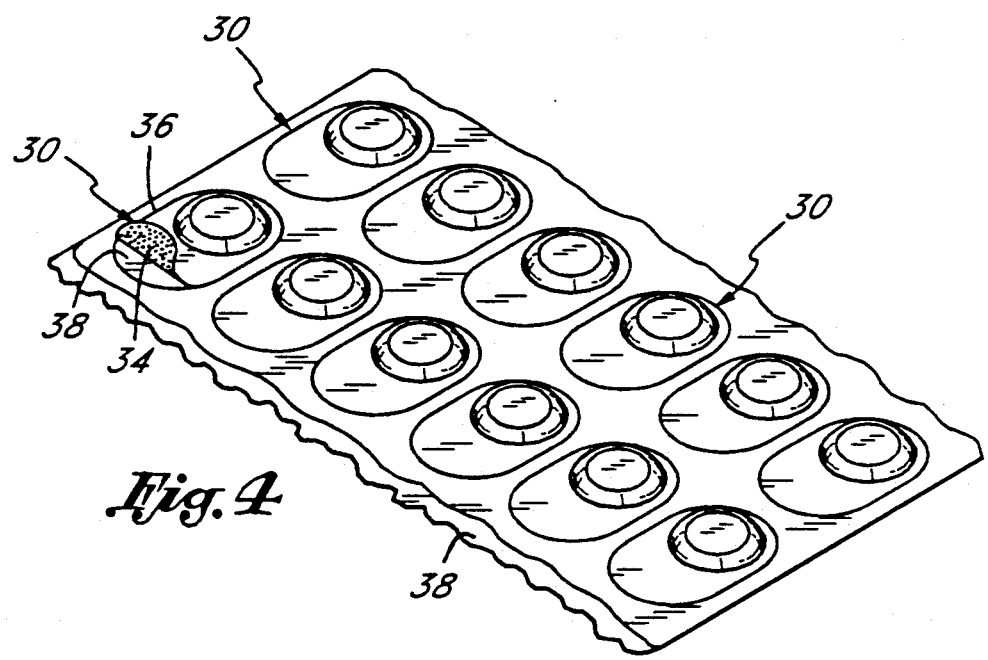

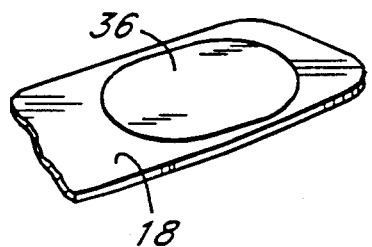
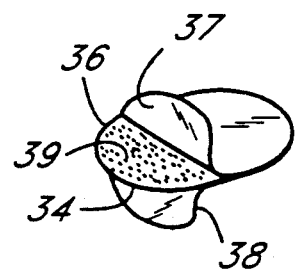
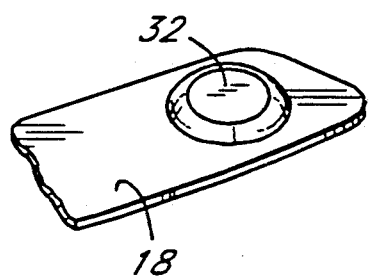
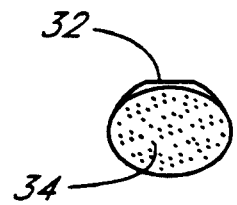
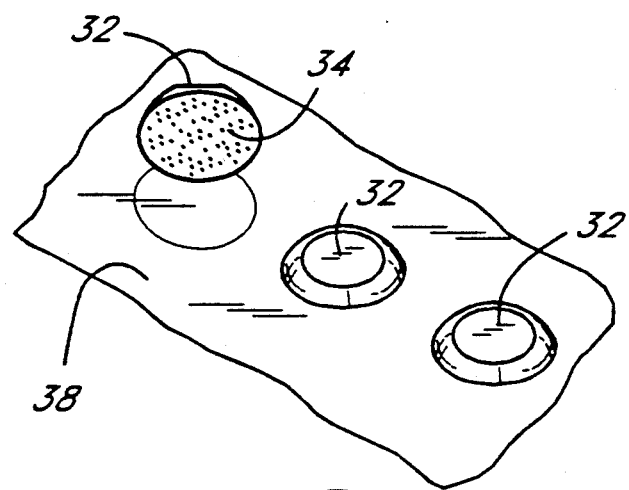

DENTAL IMPRESSION PADS AND METHOD OF MANUFACTURE

BACKGROUND OF THE INVENTION

The present invention relates to dental instruments, methods and materials used to register jaw positions and to measure or record a patient's bite. In particular, the invention relates to a system for applying and removing dental impression material on bite forks, bite trays or other dental devices.

In simulating the jaw position and the alignment of a patient's teeth, dentists usually mount dental casts or molds of the patient's teeth in a dental articulator (jaw simulator). To produce an accurate simulation, the dental casts must be positioned to a standard or predetermined reference plane taken on the patient's head when the casts are mounted in the articulator. When positioning the casts in a jaw simulator, one required step is to form impressions of the biting surface of the patient's teeth or ridges on tools known as bite forks and bite trays. Bite forks and bite trays are generally thin plate-like carriers in the shape of a row of teeth. Such bite forks and trays or other such devices, when considered collectively, will be, for convenience, referred to as dental trays herein. Impressions of the biting surfaces of the patient's teeth are made in a soft bite impression material which has been attached to the dental tray. The bite impression material then hardens.

In practice, the bite impression material is usually applied by hand directly onto the dental tray. Typically, an impression material such as sealing wax is melted onto the dental tray by placing the end of a rigid stick of wax into a flame, such as that provided by a bunsen burner. As the end of the stick starts to melt, the material is dripped onto a clean, warm and dry dental tray in the desired areas. Normally, three small mounds of wax are formed on the top and also the bottom sides of the dental tray in this manner. The tray is sometimes roughened or has holes in the areas where the bite impression material is to be deposited to cause the bite impression material to adhere tightly to the tray. The wax becomes hard at room temperature, but the wax will melt and flow or drip when heated to about 200° F. At a temperature of about 120°-140° F., it is soft and can be placed in the patient's mouth and used for obtaining an impression of the teeth, after which the impression material will accurately harden at body temperature.

After the dental tray has been used for its intended purpose and the impressions are no longer needed, the bite impression material is usually removed so that the dental tray may be reused. Removing the impression material is a difficult operation because it cannot simply be scraped away. For dental trays which mount the impression material in grooves or holes on the tray, removing the material is even more difficult. To remove the material, it is necessary to reheat the dental tray to soften and melt the material to be able to scrape it away. Both the application and removal of the impression material are time-consuming operations, which are usually done by a dentist or a highly paid assistant. Also, the task is unpleasant and somewhat dangerous because the flame and the hot wax involved often catch fire, splatter hot material and produce toxic fumes. Moreover, fuel and other clean-up supplies are wasted in applying and removing the bite impression materials.

Alternate methods and devices have been developed to eliminate the dangers and waste associated with the application and removal of the bite impression materials from dental trays. For example, dental bite forks have been made of disposable plastic with the impression materials deposited on the forks during the manufacturing process. After use, the entire fork with the impression material on it is simply discarded. However, these disposable plastic bite forks are too flexible. Bite forks should be very rigid for accurate registration of the teeth positions and for alignment of the dental casts in an articulator. Additionally, utilizing disposable plastic bite forks is expensive, since the tray and the impression material are used only once. Zinc oxide eugenol paste, as well as many other dental impression materials are also often used on bite trays. Most of these materials are difficult to clean from the tray.

Another method used to avoid the high costs that accompany applying and removing bite impression materials is the use of paraffin wax. This method wraps warm thin sheets of such wax around both sides of the dental tray. Although such wax is relatively cheap, it is difficult to make accurate impressions and the wax does not always firmly adhere to the dental tray. In addition, remnants of wax often remain on the dental tray after cleaning, which may prevent adequate sterilization after use. Unless strong, toxic chemicals are used or the wax is burned off, which both produce toxic fumes, it is difficult to remove all traces of contaminated wax from the dental tray used for previous patients.

SUMMARY OF THE INVENTION

The present invention advantageously overcomes these problems by providing an improved dental impression pad and method of manufacture. In a preferred embodiment, the dental impression pad of the present invention comprises a small mound of dental impression material such as sealing wax deposited on a thin strip of material resistant to water, heat and saliva, as well as the impression material. On the opposite side, the strip has an adhesive applied for demountable attachment of the strip to the dental tray. The adhesive is protected until use by a protective sheet that releasably attaches to the adhesive.

The impression material in solid form can be glued directly to the tray rather than melted thereon. Also, the thin strip of backing material may be glued to a tray and the impression material glued to the backing strip in solid form, or melted on, or added as a paste or putty to the backing strip.

The present invention also includes a method for manufacturing dental impression pads. In a preferred embodiment, the method of manufacture comprises the steps of: (1) applying adhesive and a protective sheet to a backing of durable plastic, such as Mylar ®; (2) cutting the backing into strips shaped to fit a section of a dental tray; (3) depositing a small amount of moldable impression material on each of the strips; (4) shaping the impression material on each of the strips to a predetermined height; and (5) solidifying the impression material.

It is an object of the present invention to provide a dental impression pad that can be easily applied to and removed from a dental tray. The present invention advantageously eliminates the need for heating the dental impression material to apply or remove it from a dental tray. With the present invention, the dental impression pad with the impression material on one side is peeled from the protective sheet, and placed on the dental tray. Similarly, the pad containing the impression material may be removed from the dental tray after being used by simply peeling the used strip with the impression material off the dental tray.

It is another object of the present invention to provide a disposable dental impression pad for sanitary purposes.

It is a further object of the present invention to provide a disposable dental impression pad that is inexpensive.

It is yet another object of the present invention to provide a thin self-adherent backing strip for dental trays so that dental impression materials will not contact the tray directly, and after usage the deposited materials can be easily removed by peeling off the strip, including the impression material.

It is still a further object of the present invention to provide a method of easily making dental impression pads in mass quantities.

BRIEF DESCRIPTION OF THE DRAWINGS

FIG. 3 is an exploded perspective view of the elements of FIG. 2;

FIG. 4 is a perspective view of a preferred embodiment of the dental impression pads of the present invention packaged before application to the bite fork;

FIG. 8 is a perspective view of the removable strip of FIG. 2 mounted by itself on a portion of a bite tray;

FIG. 9 is a perspective view illustrating the strip of FIG. 8 with adhesive and a backing sheet on each face;

FIG. 10 is a perspective view of a solid pad of impression material glued directly to a portion of a tray;

FIG. 11 is a perspective view of the pad of FIG. 10 by itself with adhesive on its flat side;

FIG. 12 is a view of pads of FIG. 4 with their adhesive covered by a releasable protective sheet.

DESCRIPTION OF THE PREFERRED EMBODIMENT

Figure 1:
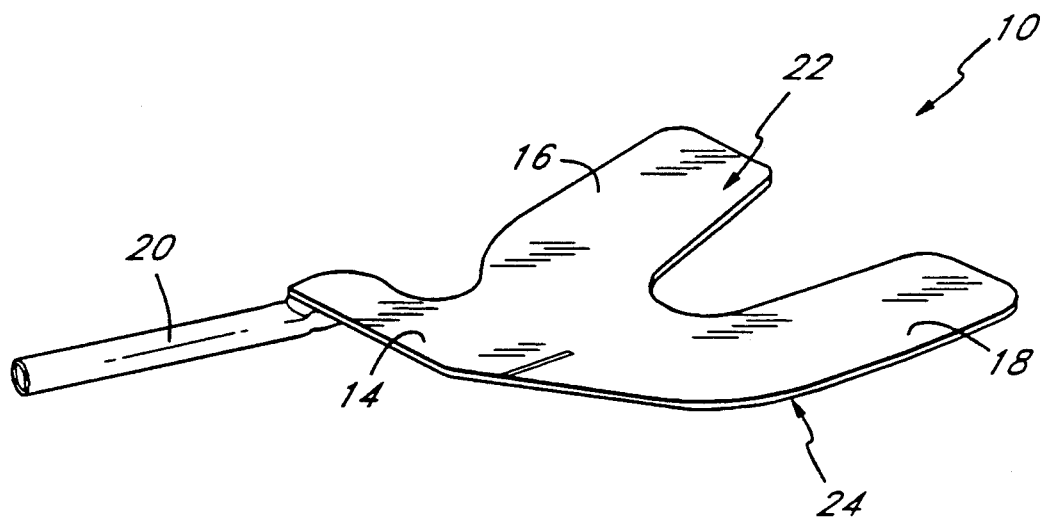
FIG. 1 is a perspective view of a typical bite fork known in the art.

As illustrated in FIG. 1, a bite fork 10, as known in the art, is a plate or tray of rigid material such as metal, preferably stainless steel. A base 14 of the bite fork 10 extends in a generally perpendicular direction from a pair of legs 16 and 18 that give the bite fork 10 a generally U-shape or horseshoe shape. Additionally, a handle 20 is attached to the base 14 and extends away from the legs 16 and 18. The handle 20 supports the bite fork 10 when it is inserted into the patient's mouth and when mounting dental casts in the articulator.

Figure 2:
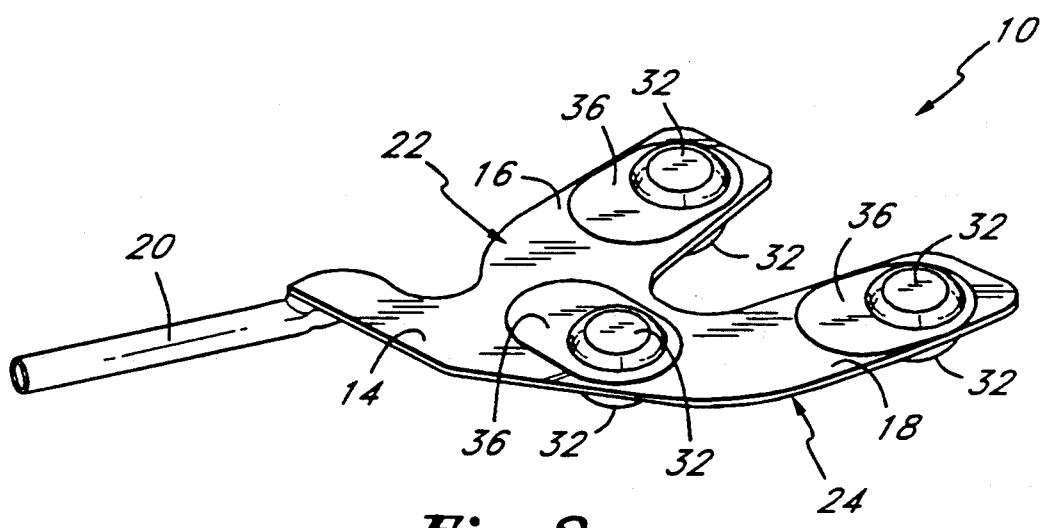
FIG. 2 is a perspective view of a preferred embodiment of dental impression pads of the present invention mounted on the bite fork.

Referring to FIG. 2, the preferred embodiment of the present invention utilizes a plurality of dental impression pads 30 attached on the bite fork 10. Three dental impression pads 30 are placed on a top side 22 of the bite fork 10 and three pads 30 are located on a bottom side 24 of the bite fork 10. One pad 30 on the top side 22 is located near the center of the bite fork 10 where the base 14 and legs 16 and 18 meet. The other two pads 30 are located on the legs 16 and 18 of the bite fork 10. The three pads 30 on the bottom side 24 of the fork 10 are similarly positioned with one pad 30 located near the center of the fork 10 and one pad 30 on each of the legs 16 and 18. The dental impression pads 30 are advantageously located to capture reliably an impression of the bite of the patient.

In a preferred embodiment each of the dental impression pads 30 further comprises a small mound or pad of dental impression material 32, an adhesive 34, a backing strip 36 and a protective sheet 38. The impression material 32 is made of a substance that is molten when heated to approximately 200° F., is soft for use in the mouth at about 120°-140° F., and is hard at body temperature. The substance does not significantly expand when heated to its softened form. Thus, an impression of the patient's bite may be made by having the patient bite into the dental impression material 32 in its softened state and allowing the dental impression material 32 to harden. The dental impression material 32 may be made of many substances including molding, modeling or denture compounds, zinc oxide eugenol paste, silicon, plastics, wax, self cured or light cured resin, etc. Some of these materials are initially soft at room temperature and then are cured to harden by heat, light, chemical, etc. In an exemplary embodiment, the dental impression material 32 is sealing wax, which is essentially like that used to seal important envelopes or documents. The dental impression material 32 initially has a flat shape which makes a clear impression of the patient's teeth when the impression material 32 is deformed vertically and outwardly by the patient's bite.

The dental impression material 32 is heated and applied in liquid form to the backing strip 36. When the dental impression material 32 is heated it will readily stick to the surface upon which it is placed. Thus, the present invention advantageously does not require glue to fasten the dental impression material 32 to the strip 36. However, to more securely fasten the impression material 32 to the strip 36 a permanent adhesive may be placed on the strip 36 before the impression material 32 is melted onto the strip 36.

The strip 36 preferably has a generally oval or racetrack shape with the impression material 32 being positioned near one end and the other end serving as a tab 42. Since the strip 36 is racetrack shaped the impression material 32 may be placed at either end and the uncovered end will be able to function as the tab 42. The tab 42 is an integral part of the backing strip 36 and provides easy mounting and removal of the dental impression pads 30 on the bite fork 10. Advantageously, the backing strip 36 is sized so it does not extend beyond the edge of the bite fork 10 and avoids contact with the patient's lips, cheek or tongue. The backing strip 36 is a thin layer of material that is resistant to heat up to 200° F. because the material is subjected to melted wax, and to water because the dental impression pad 30 and the bite fork 10 are placed in heated water to soften the dental impression material 32. Also, the material should be strong laterally to ensure accurate positioning on the bite fork 10, and sufficiently strong to withstand installation and removal from the fork 10. In a preferred embodiment the backing strip 36 is made of Mylar ®, Nylon ® or tin foil or aluminum foil. It is also advantageous to use Mylar ® for the strip 36 because lines and other information may be printed on it. In an exemplary embodiment, the backing strip 36 of the present invention is approximately one inch long, one-half inch wide and 0.003" thick.

Preferably, the backing strip 36 extends outwardly slightly beyond the periphery of the dental impression material 32 so that the dental impression material 32 does not reach the edge of the strip. The impression material 32 is located near an end of the strip 36, spaced slightly from the strip edges. The placement of the dental impression material 32 in this manner is advantageous because when impressions are made, the dental impression material 32 tends to be squeezed or flattened outwardly beyond its original shape so that some of the softened dental impression material 32 would be pressed directly onto the bite fork 10 if the backing strip 36 did not extend outward as just described.

The bottom side of the backing strip 36 is coated with the adhesive 34 for attachment to the bite fork 10, as illustrated in FIGS. 3 and 4. The adhesive 34 is a suitable glue which can withstand the temperatures involved in softening the dental impression material 32. Also, the glue is not water soluble since the sealing wax 32 will be often softened by being placed in hot water. Moreover, the adhesive 34 should be relatively easy to remove from the bite fork 10 by applying a force lifting the strip away from the tray. On the other hand, the adhesive 34 must be sufficiently strong in the direction away from the tray flat surface and must have the holding power to accurately retain the backing strip 36 in a fixed lateral position for accurately positioning dental casts or molds. In a preferred embodiment, the adhesive 34 is applied to the backing strip 36 when the dental impression pad 30 is being manufactured. Once the adhesive 34 is applied to the backing strip 36, the protective sheet 38 is placed over the adhesive 34 and the bottom side of the backing strip 36. Thus, when the dental impression pad 30 is to be used, the strip 36, the adhesive 34 and the dental impression material 32 are lifted away from the protective sheet 38 using the tab 42. Then the dental impression pad 30 is simply pressed on the bite fork 10. Suitable strip and adhesive material is commercially available in the form of rolls of Mylar ® tape or sheet, precoated with adhesive covered by a protective sheet.

Figure 5:
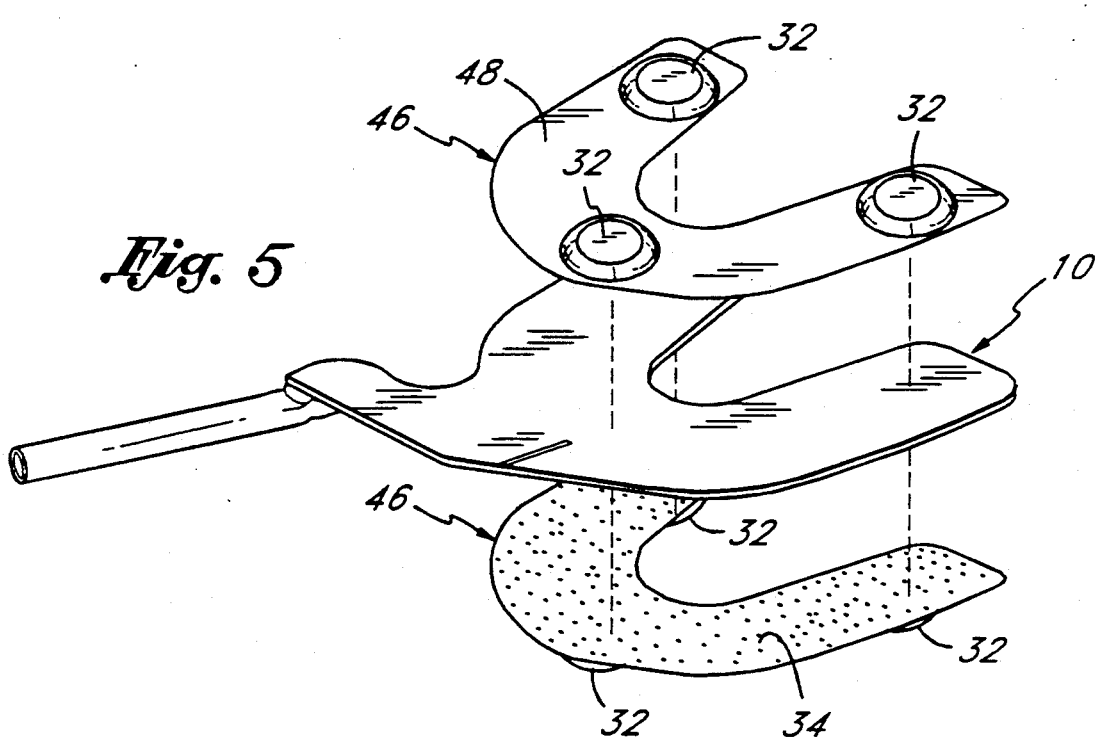
FIG. 5 is an exploded perspective view of a second embodiment of the dental impression pad of the present invention.
Figure 5A:
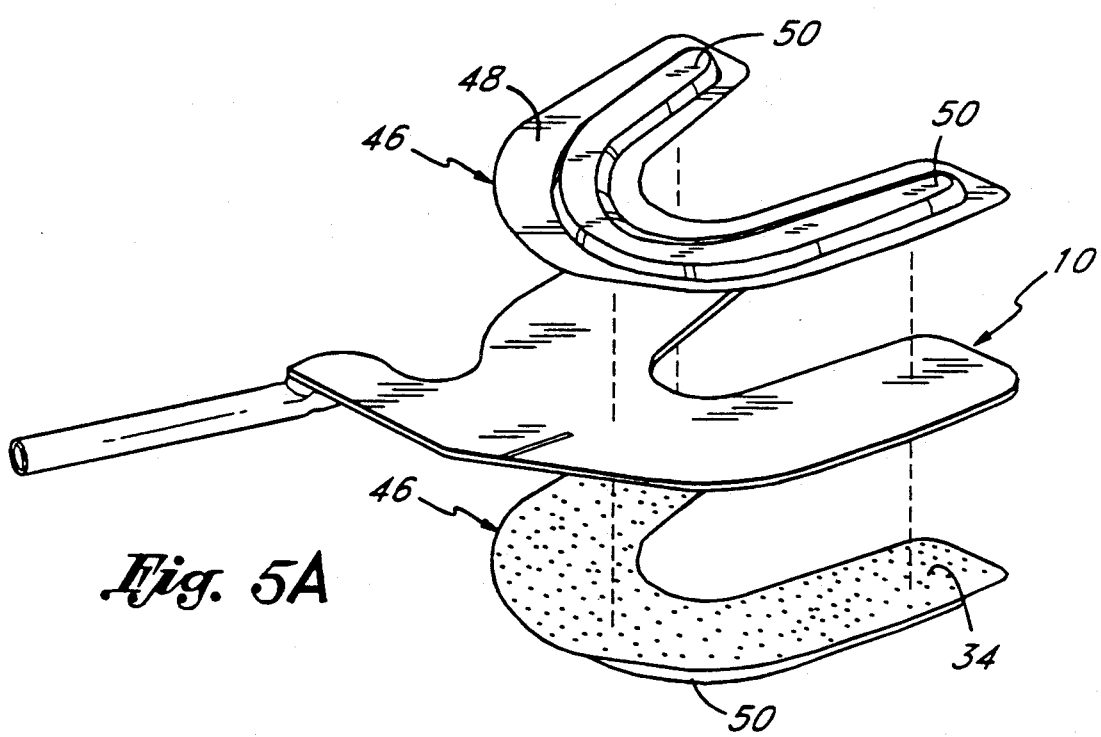
FIG. 5A is an exploded perspective view of the second embodiment of the present invention with an alternative impression material.

In a second embodiment illustrated in FIG. 5, a backing strip 46 may be U-shaped or horseshoe shaped to generally conform to the shape of the bite fork 10. The alternate backing strip 46 is the same in thickness and composition as the preferred embodiment of the backing strip 36 and varies only in shape. Also, the strip 46 has the same type of adhesive 34 and protective sheet 38 attached. This embodiment is particularly advantageous because the strip 46 covers most of the surface of the bite fork 10 thereby separating or insulating the bite fork 10 from the patient's saliva. Protecting the bite fork 10 from saliva makes this form desirable for sanitary purposes. As illustrated in FIG. 5, the backing strip 46 has three small mounds of dental impression material 32 mounted on its top side 48. The mounds of dental impression material 32 are spaced along the backing strip 46 so that they will have positions on the bite fork 10 similar to the positions of the dental impression pads 30 in FIG. 2. As a further alternative, a continuous layer 50 of the dental impression material 32 in the U-shape of the bite fork 10, as shown in FIG. 5A, can be positioned on the backing strip 46 instead of the three mounds of dental impression material 32. When the backing strip 46 is utilized, only two strips 46 are needed to position a total of six pieces of dental impression material 32 or two continuous layers 50 on the bite fork 10. Two strips 46 could also be formed as one H-shape which would be wrapped onto the tray with the upper half of the strip being placed on one side of the tray and the other half being applied to the other side.

Figure 6:
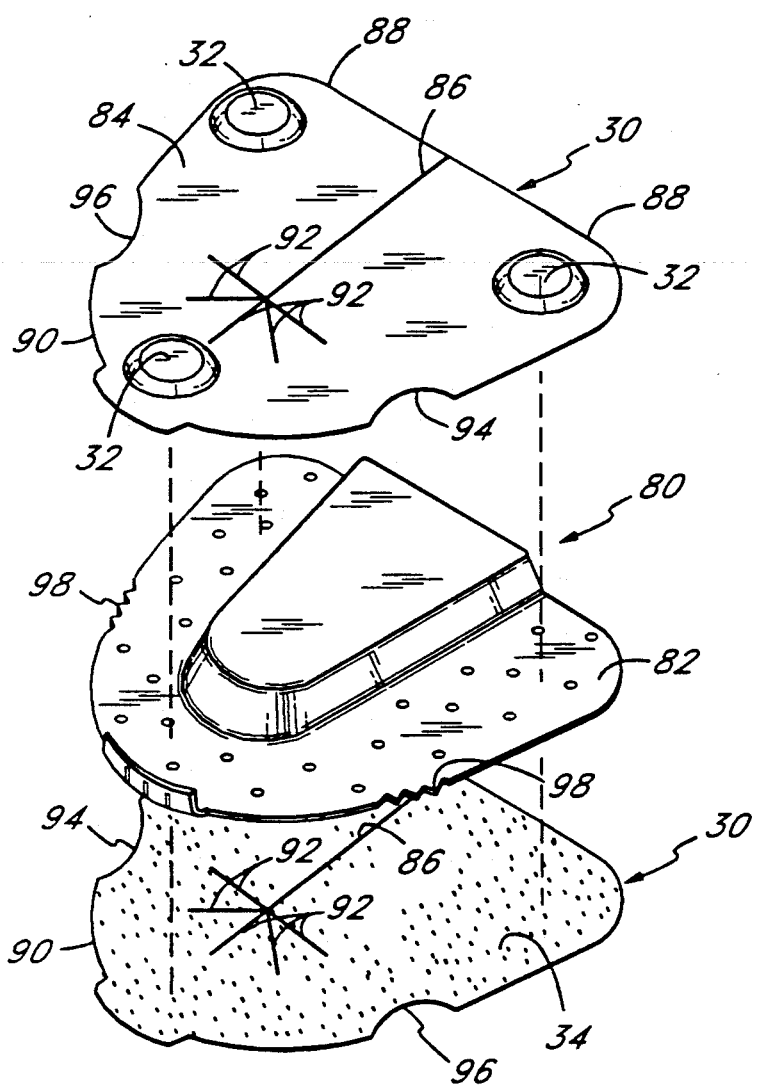
FIG. 6 is an exploded perspective view of a third embodiment of the dental impression pad of the present invention with a bite tray.
Figure 7:
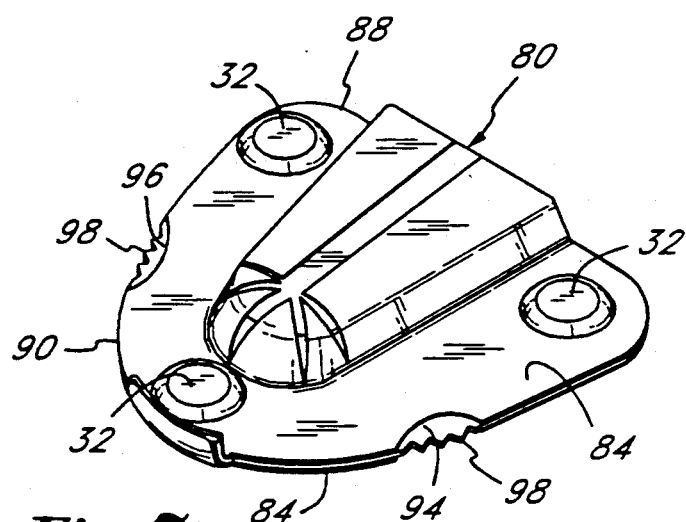
FIG. 7 is an assembled perspective view of the elements of FIG. 6.
Figure 13:
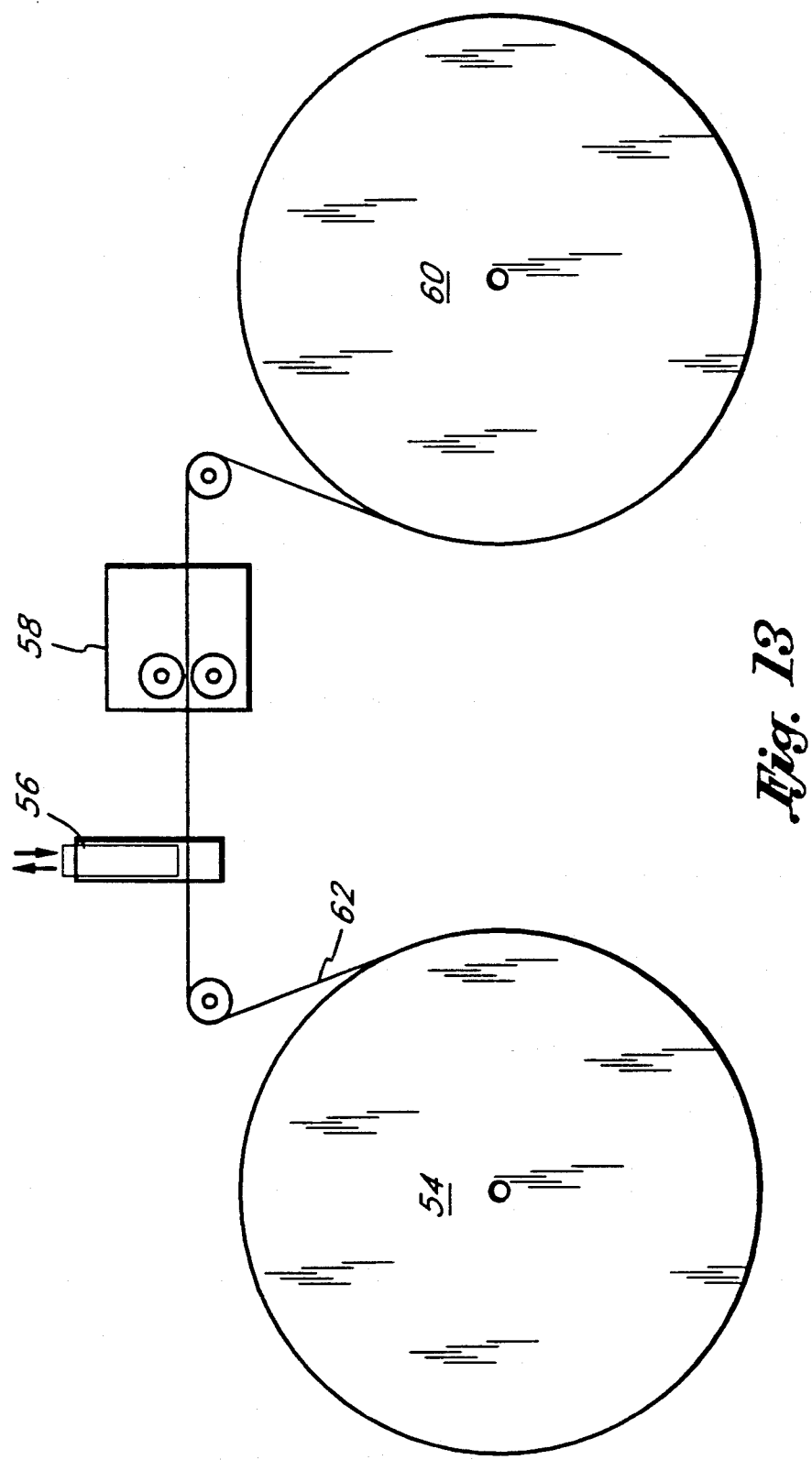
FIGS. 13 and 14 are schematic representations of the preferred manufacturing process for the dental impression pads of the present invention.

A third embodiment of the dental impression pad 30, illustrated in FIGS. 6 and 7, shows that the present invention may be used with a dental bite tray 80 known in the art. Such dental trays 80 are described in more detail in U.S. Pat. Nos. 4,543,062 and 4,693,683 to Lee. The dental tray 80 is a semicircular plate with a U-shaped bite section 82 defining an upward arch. As seen in FIGS. 6 and 7, the third embodiment of dental impression pad 30 comprises the adhesive 34, dental impression material 32 and a backing strip 84. The adhesive 34 and dental impression material 32 may advantageously take the same composition and structure as used in the second embodiment. However, the backing strip 84 of the third embodiment has a structure adapted for use on the dental tray 80. While the backing strip 84 may be constructed of Mylar ® or material with similar properties just as previous embodiments, the backing strip 84 has a distinct shape as in FIG. 6. The backing strip 84 has a generally semicircular shape and is sized to cover the tray 80. The backing strip 84 has a slit 86 along its symmetrical axis that extends from the straight edge 88 towards the curved edges 90. There are additional slits 92 in the backing strip 84 extending radially outward to the curved edges 90 from the end point of the slit 86 on the symmetrical axis. These slits 86 and 92 accommodate the upward arch of the dental tray 80 and allow the backing strip 84 to cover the full area of the bite section 82 as in FIG. 7. The slits 86 and 90 advantageously allow the backing strip 84 to conform to the shape of the dental tray 80 irrespective of whether the strip 84 is applied to the bottom or top of the tray 80. The slits 86 and 92 allow the area of the backing strip 84 covering the upward arch to be bent either upward or downward as needed according to the position of the strip 84. Furthermore, the backing strip 84 is sized to fit the dental tray 80 with two notches 94 and 96 removed from the strip 84 so that the serrated edges 98 on opposite sides of the outer edge of the bite section 82 remain accessible. This is beneficial since the serrated edges 98 are critical in the use of the bite tray 80. As with second embodiment, the dental impression material may be three small mounds 32 as in FIG. 6 or the dental impression material may be a continuous U-shaped layer 50 of impression material on the area of the backing strip 84 similar to the impression material of the second embodiment shown in FIG. 5A.

The system of the present invention greatly simplifies the mounting and removal of dental impression material on a dental tray 10 or 80. To mount the preferred embodiment of the pads 30 on the dental tray 10 or 80, the user simply removes one dental impression pad 30 from the protective sheet 38 using the tab 42 as shown in FIG. 4. The dental impression pad 30 is then placed on the dental tray 10 or 80 in the position desired with the bottom side of the backing strip 36 facing the dental tray 10 or 80 as illustrated in FIG. 3. Pressure may be applied to the pad 30 to ensure the portion of the strip 36 under the impression material 32 sticks to the dental tray 10 or 80. Advantageously, the tab 42 may remain partially unattached. This makes the pad 30 easy to remove after an impression has been made and used. The user continues to remove additional dental impression pads 30 from the protective sheet 38 and apply them to the dental tray 10 or 80 until the appropriate number of pads 30, typically six, has been mounted on the tray 10 or 80.

After the dental impression pads of sealing wax have been mounted, the tray and the pads are usually placed in a bath of water of about 120°–140° F., for a few minutes until the impression material is soft and moldable. Then the tray is removed from the bath and positioned in the mouth of the patient. The patient bites into and the impression material 32 on the tray to make an impression of his bite. The dental tray is removed from the patient's mouth and the impression material 32 is allowed to fully harden. The tray and the impressions formed in the hardened impression material 32 can now be used with an articulator to position casts of the patient's teeth and simulate jaw movement.

Once the dental tray and dental impression pads 30 have been used, the pads can be removed as easily as they were applied. To remove the pads from the tray, the user simply lifts the backing strip 36 using the tab 42. The tab 42 may be lifted or scraped away from the tray 10 or 80 using one's fingernail or a knife-like instrument. Using the lifted portion of the tab 42, the remainder of the backing strip 36 that is attached to the dental tray 10 or 80 can be removed from the dental tray 10 or 80 along with the mound of dental impression material 32 that contains the dental impression. The backing strips 46 and 84 can be similarly removed. However, with these backing strips 46 and 84, three pieces or the entire layer 50 of dental impression material are removed with each strip 46.

As illustrated in FIG. 8, the thin flexible strip 36 of FIG. 2 may be simply glued to a bite tray by itself, without any impression material on it. The glue can be applied directly to the tray 10 or 80, or to the strip at the time of mounting. Preferably, however, the strip is initially provided with a layer of adhesive 34, which may be protected by a releasable sheet 38. The strip 46 of FIG. 5 can be similarly mounted by itself. Using this approach allows the dentist to place a desired impression material on the strip with glue or with self-adhering impression material. This approach also facilitates cleaning and sanitation of the tray.

Alternatively, a solid mound or pad of impression material 32 may be glued directly on a tray, without a flexible backing strip, as viewed in FIG. 9. Again, the glue may be applied to the tray or the pad at the time of mounting, or preferably the pad is initially provided with a layer of adhesive 34 on its flat side, as viewed in FIG. 10. The adhesive, in turn, may be protected initially by a releasable sheet 38, as seen in FIG. 11. Direct gluing without the strip 36 may be slightly less convenient in that some of the impression material might flow onto the dental tray 10 or 80 area uncoated by adhesive, when the dental impression is made. Such overflow, however, would not be difficult to remove since the dental tray, having been immersed in warm water to soften the impression material, is lubricated with the water, which prevents the impression material from adhering to the bite fork except in the original area where the adhesive was placed on the impression material.

As illustrated in FIG. 4, the pads 30 may be produced on the protective sheet 38 in rows of six. As schematically shown in FIG. 12, the method of manufacture starts with a roll 54 of a laminated sheet 62 formed from a continuous layer of Mylar ® material, with a coating of adhesive 34 covered by a continuous layer of protective sheet 38. As the laminated sheet 62 passes under a cutter 56, the Mylar ® layer is "kiss" cut into rows of six backing strips 36 having the preferred form as described above. The cutter 56 advantageously "kiss" cuts only the layer of Mylar ® backing sheet leaving the layer of protective sheet intact. Next, an adhesive dispenser 58 applies a spot adhesive to each of the backing strips 36 in the area where impression material 32 is to be applied. The laminated sheet 62 may then be wound into a roll 60, or may be subjected directly to the steps as illustrated in FIG. 9. Since the protective sheet is releasable, it will not stick to the adhesive nor prevent the roll 60 from later being unrolled.

Figure 14:
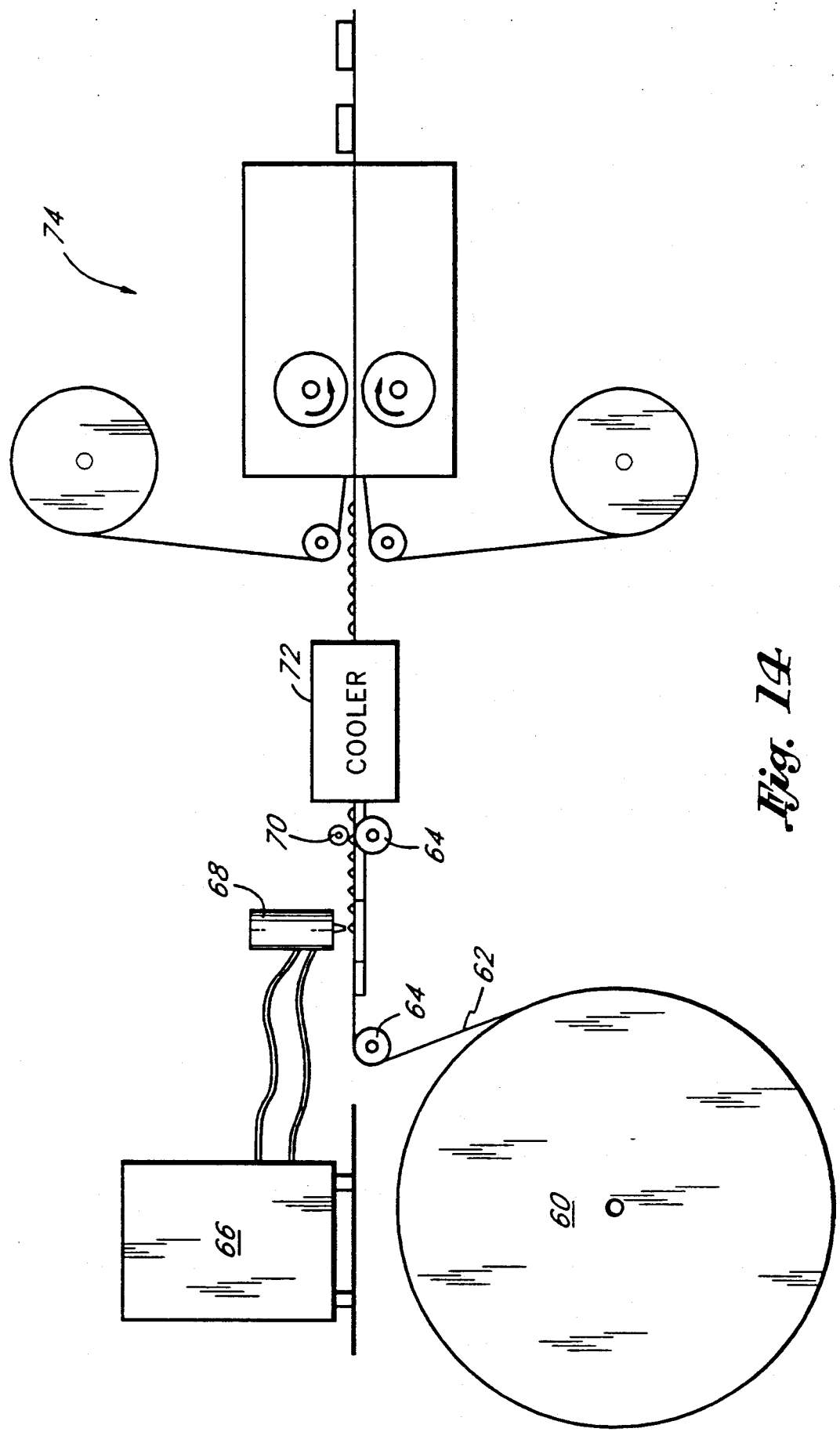

As illustrated in FIG. 14, the roll 60 of laminated sheet 62 has permanently been "kiss" cut in the oval shape and had adhesive 34 applied as the material is unrolled and directed across the rollers 64 for placement of dental impression wax on the layer of strips 36. A dispenser 66 is used to melt the wax compound. The compound flows from the dispenser 66 to a multiple jet applicator 68 which dispenses six small mounds of wax or other impression material 32 on the strips 36 as the laminated sheet 62 moves at intervals beneath the applicator 68. The sheet 62 is then moved forward and another six mounds of dental impression material 32 are deposited on the sheet 62. This process continues as the roll 60 of laminated sheet 62 is fed across the rollers 64. It should be noted that instead of applying the spot of adhesive after first cutting the strips 36 in oval form, as discussed above, suitable adhesive may be dispensed onto the strips 36 just before the impression material 32 is dispensed onto the strips 36.

After the sealing wax has been placed on the laminated sheet 62, the sheet 62 passes under a thickness control roller 70 which flattens the mounds of soft impression material 32 to a preferred thickness. The roller 70 is applied to mold the thickness of the sealing wax immediately after it is applied, since the wax is still warm and moldable. Once the mounds of wax have been flattened, the laminated sheet 62 and mounds of sealing wax pass through a cooler 72. The newly formed dental impression pads 30 are cooled so that the sealing wax will harden in its preferred shape until reheated before insertion into the patient's mouth. After the sealing wax is cooled and set, the sheet 62 may be cut by a cutter 74 into convenient sections 38 and packaged for sterility, containing, for example, 36 dental impression pads 30.

Having described the invention in connection with certain preferred embodiments thereof, it will be understood that many modifications and variations thereto are possible, all of which fall within the true spirit and scope of this invention.

WHAT IS CLAIMED IS:

1. A dental impression pad for use with a dental tray for making a dental impression comprising:
    a strip of thin material;
    an adhesive covering one side of said strip; and
    dental impression material attached on a second side of said strip.

2. The pad of claim 1, further comprising a protective sheet releasably attached to said strip by said adhesive.

3. The pad of claim 2, further comprising adhesive affixing said impression material to said strip.

4. The pad of claim 1, wherein said adhesive can withstand the temperatures of heating said impression material and is resistant to water, saliva and dental impression material.

5. The pad of claim 1, wherein said strip is made of Mylar ® material, plastic, aluminum foil, tin foil or paper.

6. The pad of claim 1, wherein said strip can withstand the temperatures of heating said impression material, and is resistant to water, saliva, and dental impression material.

7. The pad of claim 1, wherein said impression material is spaced from the periphery of said strip so that said impression material will not extend beyond said strip and contact the dental tray when a dental impression is made.

8. The pad of claim 1, wherein said impression material is a small mound of sealing wax.

9. The pad of claim 1, wherein said strip has a generally oval or racetrack shape.

10. The pad of claim 9, wherein said impression material is positioned on one end of said strip and the other end of said strip forms a tab to facilitate gripping, positioning and removing the pad from the dental tray.

11. The pad of claim 1, wherein said strip is sized for placement on the center or legs of a dental tray.

12. A combination for making a dental impression comprising:
a dental impression material; and
an adhesive for attaching said material to a dental tray wherein said impression material is in the form of a small pad which is hard at room temperature and has a flat surface for facilitating mounting on a flat surface of said dental tray, with said adhesive being on said flat surface of said pad.

13. The combination of claim 12, including a dental tray attached to said material by said adhesive.

14. The combination of claim 13, including a strip of material resistant to water, heat, saliva and dental impression material attached to said impression material on one side and attached to said dental tray by said adhesive on its other side.

15. The combination of claim 12, comprising a flexible strip attached to one side of said impression material and a protective sheet attached to said strip by said adhesive, said protective sheet being removable for attachment of said strip and said impression material to said dental tray.

16. The combination of claim 12, wherein said adhesive is resistant to water, saliva, dental impression materials and the heat of softening said materials.

17. The combination of claim 12, including a flexible strip attached to one side of said impression material, and wherein said impression material is spaced from the periphery of said strip so that said impression material will not extend beyond said strip nor contact said dental tray when a dental impression is made.

18. The combination of claim 17, wherein said strip of material has a substantially semicircular shape and one or more slits for facilitating applying said strip to a dental tray which is not completely flat.

19. The combination of claim 17, wherein said strip of material has a substantially U-shape similar to the shape of said dental tray.

20. The combination of claim 19, wherein said impression material is a continuous U-shaped layer of sealing wax.

21. The combination of claim 19, wherein said impression material comprises at least three small mounds of material spaced along said strip.

22. The combination of claim 12, wherein said adhesive will permit solid impression material to be removed as a unit from a dental tray by prying with a fingernail or knife-like tool.

23. The combination of claim 12, wherein said impression material is solid, and including a protective covering on said adhesive.

24. A combination for making dental impressions with a dental tray comprising:
a backing;
a layer of adhesive covering one side of said backing;
an adhesive protecting sheet releasably attached to said backing by said adhesive;
a plurality of strips cut in said backing but remaining attached to said protective sheet by said adhesive; and
a plurality of dental impression pads attached on a second side of said backing.

25. The combination of claim 24, wherein said backing is made of strong, thin, flexible material which is resistant to water, heat, saliva and dental impression material.

26. The combination of claim 24, wherein said backing is made of Mylar ® material and said pad is sealing wax.

27. The combination of claim 26, wherein each of said strips has a tab to facilitate the removal of said strip together with said pad from said protective sheet, the positioning of said strip and said pad on the dental tray, and the removal of said strip and said pad from said dental tray.

28. A method for applying a dental impression material to a dental tray comprising the steps of:
removing a releasably attached protective sheet from a dental impression pad to expose adhesive attached to the dental impression pad; and
attaching the dental impression pad in a desired location on the dental tray by pressing the adhesive side of the dental impression pad onto the dental tray.

29. A method for making a dental impression comprising the steps of:
removing a protective sheet from a dental impression pad to expose adhesive attached to said pad;
positioning said pad in a desired location on a dental tray;
giving said pad on said tray a moldable consistency suitable for making a dental impression;
after making an impression in said pad, lifting an edge of a strip of said pad away from said tray; and
removing the remaining portion of said strip of material using said edge.

30. A method for manufacturing dental impression pads used with dental trays comprising the steps of:
detachably mounting a protective sheet to a thin backing;
cutting said backing into a plurality of strips; and
applying dental impression material onto said strips.

31. The method of claim 30, wherein said applying step includes:
dispensing mounds of said dental impression material on said strips;
flattening said mounds into flat pads; and solidifying said pads.

32. A method of manufacturing dental impression pads used with dental trays comprising the steps of:
   forming dental impression material into a preferred hardened shape;
   applying adhesive to a hardened surface of said shape before placing the pad on a dental tray.

33. The method of claim 33, including forming said surface to be flat before applying said adhesive.

34. The method of claim 33, including attaching a removable protective sheet to cover said adhesive.

35. A method of applying dental impression material to a dental tray comprising:
   forming a pad of dental impression material;
   solidifying said pad; and
   gluing the pad to a dental tray with a glue which will securely hold said pad in place when said dental tray is heated to soften said impression material when dental impressions are to be made, but will permit said impression material to be easily removed from said tray.

36. A method for applying dental impression material to a dental tray comprising the steps of:
   providing a thin flexible strip adapted to receive dental impression material.
   removing a releasably attached protective sheet from said dental impression strip to expose adhesive attached to said strip; and
   attaching said strip in a desired location on the dental tray with said adhesive.

37. An article for use with a dental tray for making a dental impression comprising:
   a strip of thin material resistant to heat, water and saliva, sized to fit on a dental bite tray, said strip further being sized and adapted to receive a quantity of dental impression material;
   a first adhesive covering a first side of said strip for attaching said strip to said tray, said adhesive being resistant to water, saliva and the heat associated with making dental impressions, said adhesive being adapted to facilitate later removal of said strip and impression material from said tray.

38. The article of claim 37, further comprising a protective sheet releasably attached to one side of said strip by said adhesive.

39. The article of claim 38, further comprising a second adhesive on a second side of said strip for affixing dental impression material to said strip.

40. The article of claim 39, further comprising a second protective sheet releasably attached to said strip by said second adhesive.

41. The article of claim 37, wherein said strip is made of plastic, aluminum foil, tin foil or paper.

42. The article of claim 37, wherein said strip has a generally horse shoe shape sized to cover one side of the dental tray.

43. The article of claim 37, wherein said strip has a substantially H-shape such that said strip can be folded over an edge of said dental tray to cover both sides of said dental tray.

44. The article of claim 37 in combination with a dental tray to which said strip is releasably attached by said adhesive.

45. The article of claim 37, wherein said strip is generally oval in shape.

46. A method for applying dental impression material to a dental tray comprising the steps of:
   providing a thin flexible strip adapted to receive dental impression material.
   removing a releasably attached protective sheet from said strip to expose adhesive attached to said strip; and
   attaching said strip in a desired location on the dental tray with said adhesive.

47. An article for use with a dental tray having a flat surface for making a dental impression comprising:
   a strip of thin, flat, planar material resistant to heat, water and saliva, adapted to be attached to a flat surface on said dental tray; and dental impression material being securely attached to one side of said strip before said strip is attached to said tray.

48. The article of claim 47, further comprising adhesive affixed to the other side of said strip.

* * * * *